US012161743B2

(12) United States Patent
Hao et al.

(10) Patent No.: US 12,161,743 B2
(45) Date of Patent: Dec. 10, 2024

(54) CHLORHEXIDINE-CYCLAMATE COMPLEXES AND ORAL CARE COMPOSITIONS COMPRISING THE SAME

(71) Applicant: Colgate-Palmolive Company, New York, NY (US)

(72) Inventors: Zhigang Hao, Bridgewater, NJ (US); Chi-Yuan Cheng, Hillsborough, NJ (US); Long Pan, Somerset, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 112 days.

(21) Appl. No.: 17/695,100

(22) Filed: Mar. 15, 2022

(65) Prior Publication Data

US 2022/0192952 A1     Jun. 23, 2022

Related U.S. Application Data

(62) Division of application No. 16/955,308, filed as application No. PCT/US2017/067317 on Dec. 19, 2017, now Pat. No. 11,278,481.

(51) Int. Cl.
*A61Q 11/00*     (2006.01)
*A61K 8/02*     (2006.01)
*A61K 8/43*     (2006.01)
*A61K 8/46*     (2006.01)

(52) U.S. Cl.
CPC .............. *A61K 8/43* (2013.01); *A61K 8/0295* (2013.01); *A61K 8/466* (2013.01); *A61Q 11/00* (2013.01)

(58) Field of Classification Search
CPC ........ A61K 8/43; A61K 8/0295; A61K 8/466; A61K 47/541; A61Q 11/00; A61Q 17/005; C07C 2601/14; C07C 279/265; C07C 307/02; A61P 1/02
See application file for complete search history.

(56) References Cited

U.S. PATENT DOCUMENTS

| | | | |
|---|---|---|---|
| 4,980,150 A | 12/1990 | Keith | |
| 6,592,912 B1 * | 7/2003 | Barabolak | A23G 4/20 424/440 |
| 11,278,481 B2 * | 3/2022 | Hao | A61Q 17/005 |
| 2005/0048005 A1 | 3/2005 | Stockel | |

(Continued)

FOREIGN PATENT DOCUMENTS

| | | |
|---|---|---|
| EP | 0306455 | 3/1989 |
| WO | 1999/033352 | 7/1999 |

OTHER PUBLICATIONS

Cattaneo, Damiano et al. "Crystal structure resolution of two different chlorhexidine salts." Journal of molecular structure vol. 1121 ( 2016): 70-73. doi: 10.1016/j.molstruc.2016.04.077. (Year: 2016).*

(Continued)

*Primary Examiner* — Isaac Shomer
*Assistant Examiner* — Bryan James Rego

(57) ABSTRACT

The present disclosure provides a chlorhexidine-cyclamate complex having a formula $[C_{22}H_{32}Cl_2N_{10}][C_6H_{12}NO_3S]_2$ having antibacterial and antiplaque properties, together with oral care compositions comprising the complex, and methods of making and using these complexes and compositions.

14 Claims, 9 Drawing Sheets

(56) References Cited

U.S. PATENT DOCUMENTS

2005/0191247 A1* 9/2005 Drake ............... A61Q 11/00
424/49
2007/0274929 A1* 11/2007 Alexander ......... A61Q 11/00
424/54
2016/0130234 A1 5/2016 Ferrari

OTHER PUBLICATIONS

Lima, Ana Paula de, et al. "Electrochemical oxidation of chlorhexidine and its amperometric determination by flow-injection analysis." Journal of the Brazilian Chemical Society 25 (2014): 448-452. (Year: 2014).*
International Search Report and Written Opinion of the International Searching Authority in International Application No. PCT/US2017/067317, mailed May 28, 2018.

* cited by examiner

CHLORHEXIDINE-CYCLAMATE COMPLEXES AND ORAL CARE COMPOSITIONS COMPRISING THE SAME

CROSS REFERENCE TO RELATED APPLICATIONS

This application is a divisional of U.S. application Ser. No. 16/955,308, filed Jun. 18, 2020, which is a United States Application under 35 C.F.R. 371 claiming benefit of PCT Application No. PCT/US2017/067317, filed on Dec. 19, 2017, the entire contents of each of which are incorporated herein by reference.

BACKGROUND

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infection and dental disease associated with plaque formation. For example, biguanide and bis-biguanide compounds such as chlorhexidine are well known to the art for their antibacterial activity and have been used in oral compositions to counter plaque formation by bacterial accumulation in the oral cavity. However, it is also well known that bis-biguanide compounds, when used as dental antiplaque agents cause unsightly staining of teeth.

In order for antiplaque activity to be imparted to the surface of a tooth, the bis-biguanide must be deposited to at the surface of the tooth. This is normally achieved through brushing with a dentifrice or through swishing with a mouthwash containing the bis-biguanide. Once deposited at the surface of the tooth, the effect of the bis-biguanide on plaque is immediate. Through normal activities such as eating and drinking, the contents of the dentifrice, including the bis-biguanide are washed away, which limits the term of its effectiveness. In addition, there is often a gap of many hours between brushing or use of a suitable mouthwash, and plaque may accumulate during these interim periods.

Thus, there is a need to deposit bis-biguanides, chlorhexidine, at the surface of a tooth for an extended period of time. There is also a need to develop a vehicle for a bis-biguanide that allows it to resist being washed away in the mouth through ordinary biological means.

BRIEF SUMMARY

Chlorhexidine is known as a potent antibacterial and antiplaque agent commonly utilized in in oral care dentifrices. Sodium cyclamate is an artificial sweetener that is acceptable for use in consumer products, such as oral care compositions. The present disclosure provides a chlorhexidine-cyclamate complex, which may interchangeably be referred to herein as CHC. The chemical structure of the complex is $[C_{22}H_{32}Cl_2N_{10}][C_6H_{12}NO_3S]_2$ or $[C_{22}H_{32}Cl_2N_{10}][C_6H_{12}NO_3S]_2 \cdot H_2O$. The complex has key features that make it ideal for use in dentifrice compositions as an antibacterial or antiplaque agent.

The inventors have found that the CHC complex of the present disclosure is largely insoluble in water, and provides for an extended release profile of chlorhexidine into the oral cavity. Thus, the present disclosure provides an antiplaque agent that acts on a tooth's surface during a time period extending between brushing or use of a suitable mouthwash, so as to prevent plaque from accumulating.

The present disclosure thus provides CHC per se, as well as oral care products that deliver CHC to the oral cavity, i.e., to the surface of the teeth, and methods of making and using CHC. In one embodiment, the present disclosure provides oral care compositions that comprise CHC. As the CHC antibacterial properties, the present disclosure also encompasses other oral care compositions, for example mouth rinses or mouthwashes, comprising a CHC, e.g., any of Complex 1, et seq. and/or precursors thereof. The disclosure further provides methods of reducing plaque comprising applying the composition to a surface of a tooth, and methods of killing bacteria comprising contacting the bacteria with the composition.

Further areas of applicability of the present disclosure will become apparent from the detailed description provided hereinafter. It should be understood that the detailed description and specific examples, while indicating preferred embodiments, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description of the preferred embodiment(s) is merely exemplary in nature and is in no way intended to limit the disclosed complexes, its application, or uses.

The present disclosure therefore provides, in a first embodiment, a chlorhexidine-cyclamate complex having the formula $[C_{22}H_{32}Cl_2N_{10}][C_6H_{12}NO_3S]_2$ (sometimes referred to herein as "CHC"), e.g., 1.1. Complex 1 wherein the complex is formed from a mixture of chlorhexidine and sodium cyclamate in a molar ratio of chlorhexidine:sodium cyclamate of 1:1 to 1:3 (e.g., about 1:2).

Figure 9:
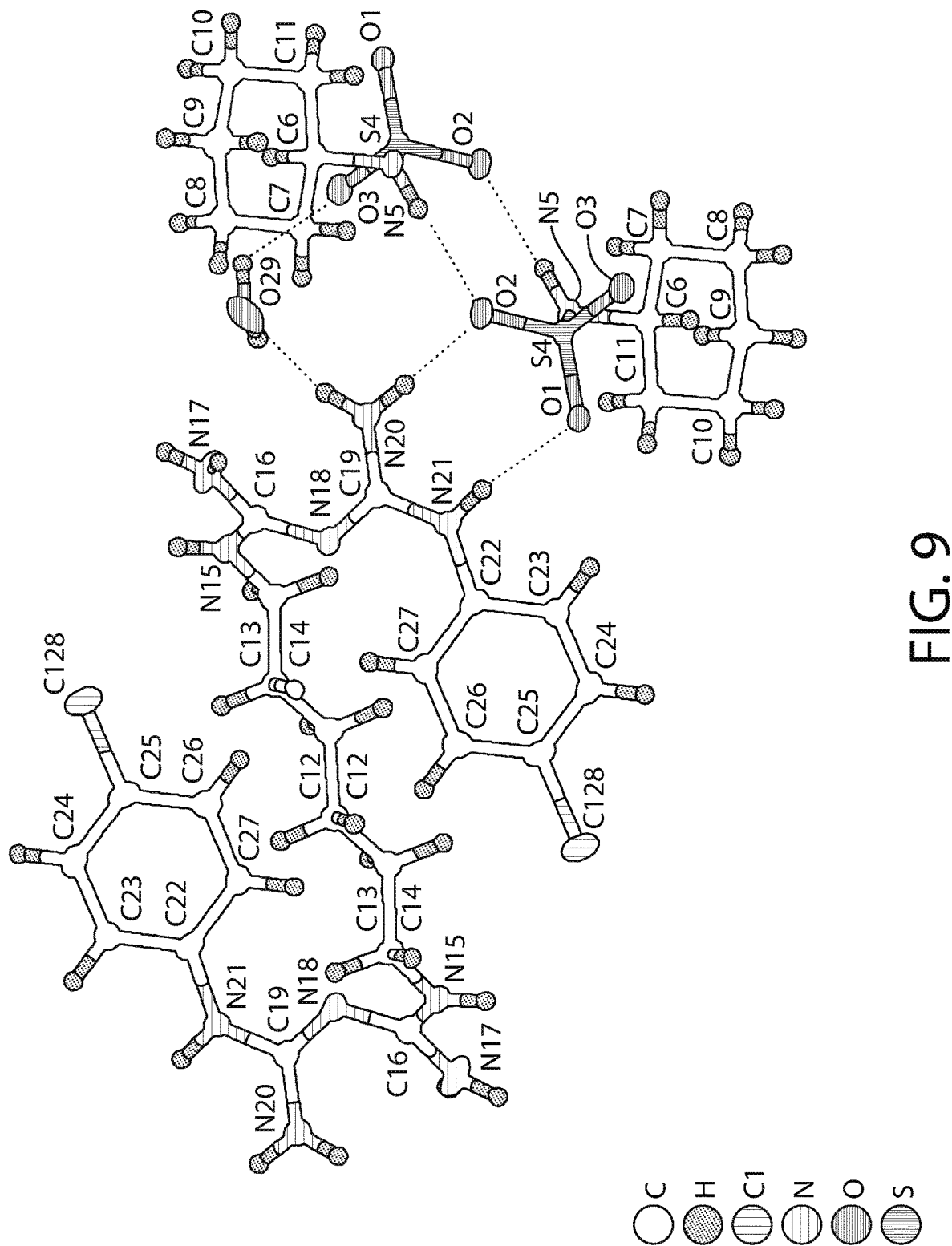
FIG. 9 depicts the crystalline structure of the chlorhexidine cyclamate complex determined by single-crystal X-ray diffraction measurement.

1.2. Complex 1 or 1.1 in crystalline form.
1.3. Any of the foregoing complexes, wherein the complex is anhydrous.
1.4. Any of the foregoing complexes, wherein the complex is in the form of a hydrate, hemi-hydrate or polyhydrate (e.g., hydrate).
1.5. Any of the foregoing complexes in the form of a hydrate.
1.6. The complex of claim 1.4 or 1.5, having the formula $[C_{22}H_{32}Cl_2N_{10}] [C_6H_{12}NO_3S]_2 \cdot H_2O$.
1.7. Any of the foregoing complexes in crystalline form in a $P2_1/c$ space group.
1.8. Any of the foregoing complexes wherein the a biguanide group in the chlorhexidine molecule is coordinated with a water molecule and two cyclamate molecules.
1.9. Any of the foregoing complexes wherein both biguanide group in the chlorhexidine molecule is coordinated with a water molecule and two cyclamate molecules.
1.10. Any of the foregoing complexes having a structure wherein a biguanide moiety of the chlorhexidine cation is coordinated by two cyclamate ligands and a water ligand as shown in FIG. 9.
1.11. Any of the foregoing complexes wherein the chlorhexidine-cyclamate complex forms a crystal in an aqueous solution.
1.12. Complex 1.8, wherein the aqueous solution contains more than 50 wt. % water, more than 60 wt. % water, more than 70 wt. % water, or more than 80 wt. % water.
1.13. Complex 1.8 or 1.9, wherein the aqueous solution contains 84 wt % water, 3 wt. % ethanol, and 10 wt. % glycerin.
1.14. Any of the foregoing complexes wherein the chlorhexidine-cyclamate complex forms as a precipitate in aqueous solution.
1.15. Any of the foregoing complexes when crystalized from aqueous ethanol.
1.16. Any of the foregoing complexes which forms a precipitate upon increasing dilution with water.

In a further embodiment, the disclosure provides an oral care composition (Composition 2) for application to the oral cavity which comprises CHC, e.g., any of Complex 1, et seq., as described above, in combination with an orally acceptable carrier. For example, the disclosure provides:

2.1 Composition 2 wherein the complex is formed from a mixture of chlorhexidine and sodium cyclamate in a molar ratio of chlorhexidine:sodium cyclamate of 1:1 to 1:3 (e.g., about 1:2),
2.2 Any of the foregoing complexes wherein the chlorhexidine-cyclamate complex forms a crystal in an aqueous solution.
2.3 Any of the foregoing complexes when crystalized from aqueous ethanol.
2.4 Any of the foregoing compositions wherein CHC is complex is formed, in whole or in part, in situ from chlorhexidine and sodium cyclamate.
2.5 Any of the foregoing compositions comprising CHC in an amount of 0.01 to 40% by weight of the composition.
2.6 Any of the foregoing compositions wherein the composition is in the form of a dentifrice, gel or mouthwash The disclosure further provides methods of killing bacteria comprising contacting the bacteria with an antibacterially effective amount of a CHC, e.g., any of Complex 1, et seq. for example contacting with e.g., any of Composition 2, et seq. In some embodiments, the disclosure also provides a method or treating, reducing or preventing plaque with an antibacterially effective amount of a CHC, e.g., any of Complex 1, et seq. for example contacting with e.g., any of Composition 2, et seq.

The disclosure further provides a method of making a complex comprising CHC, e.g., any of Complex 1, et seq. comprising combining chlorhexidine and sodium cyclamate in aqueous solution, and optionally adding this mixture to ethanol and isolating the crystalline precipitate thus obtained.

The disclosure further provides (i) the use of a CHC, e.g., any of Complex 1, et seq., to kill bacteria; (ii) the use of a CHC, e.g., any of Complex 1, et seq., in the manufacture of a composition to kill bacteria; (iii) CHC, e.g., any of Complex 1, et seq., for use in killing bacteria; (iv) the use of a CHC, e.g., any of Complex 1, et seq., in the manufacture of a composition to treat, reduce or prevent plaque; (v) the use of a CHC, e.g., any of Complex 1, et seq., in the manufacture of a composition to treat, reduce or prevent plaque; and (vi) CHC, e.g., any of Complex 1, et seq., to treat, reduce or prevent plaque.

It will be understood that, although the CHC may be primarily in the form of a complex, there may be some degree of equilibrium with chlorhexidine and sodium cyclamate precursor materials, so that the proportion of material which is actually in complex compared to the proportion in precursor form may vary depending on the precise conditions of formulation, concentration of materials, pH, presence or absence of water, presence or absence of other charged molecules, and so forth.

The composition can include the CHC, e.g., any of Complex 1, et seq. and/or precursors thereof, for example chlorhexidine and sodium cyclamate. In one embodiment, the CHC is prepared at room temperature by mixing the precursors in an aqueous solution. The in situ formation provides ease of formulation. The precursors can be used instead of first having to form the CHC. In another embodiment, the water permitting formation of the CHC, e.g., any of Complex 1, et seq. from the precursor is water that is present in the oral care composition.

In certain embodiments, the amount of CHC, e.g., any of Complex 1, et seq. in the composition of the disclosure, e.g., any of Compositions 2, et seq., is 0.01 to 40% by weight of the composition. In certain embodiments, precursors, e.g., chlorhexidine and sodium cyclamate, are present in amounts such that when combined into the CHC, e.g., any of Complex 1, et seq., the CHC, e.g., any of Complex 1, et seq. would be present in an amount of 0.05 to 10% by weight of the composition. In either of these embodiments, the amount of the CHC, e.g., any of Complex 1, et seq. can be varied for the desired purpose, such as an antibacterial agent or as an antplaque agent for extended release. In other embodiments, the amount of the CHC, e.g., any of Complex 1, et seq. is at least 0.1, at least 0.2, at least 0.3, at least 0.4, at least 0.5, at least 1, at least 2, at least 3, or at least 4 up to 10% by weight of the composition. In other embodiments, the amount of the CHC, e.g., any of Complex 1, et seq. is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In some embodiments, the total amount of chlorhexidine in the composition is 0.05 to 10% by weight of the composition. In other embodiments, the total amount of chlorhexidine is at least 0.1, at least 0.2, at least 0.3, at least 0.4, at least 0.5, or at least 1 up to 8% by weight of the composition.

As used herein, an "oral care composition" refers to a composition for which the intended use can include oral care, oral hygiene, or oral appearance, or for which the intended method of use can comprise administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

The carrier represents all other materials in the composition other than the CHC, e.g., any of Complex 1, et seq. or the chlorhexidine and sodium cyclamate. The amount of carrier is then the amount to reach 100% by adding to the weight of the CHC, e.g., any of Complex 1, et seq. or the chlorhexidine and sodium cyclamate.

For oral care compositions, the carrier can be any carrier that is used for dentifrices and mouthwashes. The carrier can be in the form of a gel or a solution.

Optional ingredients that can be included in an oral care formulation of the compositions of the disclosure include solvents; water-soluble alcohols such as $C_{2-8}$ alcohols including ethanol; humectants (e.g., glycols including propylene glycol, di propylene glycol, tripropylene glycol and mixtures thereof; glycerides including mono-, di- and triglycerides; and polyols such as sorbitol, xylitol, and propylene glycol); medium to long chain organic acids, alcohols and esters; surfactants including emulsifying and dispersing agents; structurants including thickeners and gelling agents, for example polymers, abrasives such as silicates; and colorants including dyes and pigments.

The compositions can be used in a method to kill bacteria or to treat or prevent plaque by applying the composition to the surface of the teeth (i.e. contacting bacteria or plaque with the composition). In certain embodiments, the application is with the use of a toothbrush. The application is alternatively carried out by swishing a mouthwash comprising CHC in the oral cavity. For example, in one embodiment, the combination of the chlorhexidine with the sodium cyclamate increases the duration at which the chlorhexidine is available in the oral cavity, which can then kill bacteria.

Thus, the present disclosure provides (i) a method for killing bacteria in the oral cavity comprising applying to teeth an effective amount of a formulation of any embodiment embraced or specifically described herein, e.g., any of Composition 2 et seq.; and (ii) a method for treating or reducing the formation of plaque comprising applying to teeth an effective amount of a formulation of any embodiment embraced or specifically described herein, e.g., any of Compositions 2 et seq.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the disclosure extends to the product of the combination of the listed ingredients.

EXAMPLES

Example 1—Synthesis Chlorhexidine-Cyclamate Complex CHC

An aqueous composition was created according to the formulation detailed in Table 1. was observed that the chlorhexidine-cyclamate complex formed as a precipitate.

TABLE 1

| Material | Concentration (wt. %) |
| --- | --- |
| Chlorhexidine | 0.69 |
| Sodium cyclamate | 0.09 |
| Glycerin | 9.75 |
| Sodium Fluoride | 0.05 |
| Water | 84% |
| Tween 20 | 0.30 |
| Myacide | 0.05 |
| Xylitol | 2.0 |
| Sacarina | 0.02 |
| Ethyl alcohol | 3.0 |
| Mint flavor | 0.05 |

The crystals that precipitated out of the solution were collected and subjected to further analysis, detailed below.

Example 2: Mass Spectrometric Analysis of CHC

LC-MS analysis was performed using a AB Sciex tandem mass spectrometer (AB Sciex LLC, Framingham, MA, USA) equipped with an ESI interface and Agilent 1260 capillary LC system (Model Agilent 1260, Agilent Technologies, Palo Alto, CA, USA). The capillary LC system was equipped with a capillary binary pump (Model G1376A), a DAD detector (G1315C), a micro vacuum degasser (Model G4225A), a thermostatted column compartment (Model G1316A, The capillary pump was set under the micro-flow mode. The LC separation was achieved by using an Agilent Zothax SB-Aq column with 2.1 mm i.d.×50 mm dimension and 3.5 μm particle size (Agilent Technologies, Palo Alto, CA, USA Part No. 871700-914).

The mobile phase used during the analysis was methanol. The flow rate was 70 μL/grin and the injected volume was 1 μL. The AB Sciex tandem mass spectrometer was operated in the positive-ion mode under the following conditions:

nitrogen (>99.99%) was used for curtain gas at 10 psi, ion source gas 1 and 2 at 10 and 10 psi, respectively. ESI IonSpray voltage was set at 5.5 kV in ESI interface. The declustering and entrance potential were set up at 80 and 5.5 v, respectively. The temperature of the ionization interface was maintained at 550° C. For total ion count (TIC) mode, the MS screen range was from 50 to 1000 m/z. Data was acquired with an Analyst software 1.6.2 system (AB Sciex LLC, Framingham, MA, USA).

Figure 1:
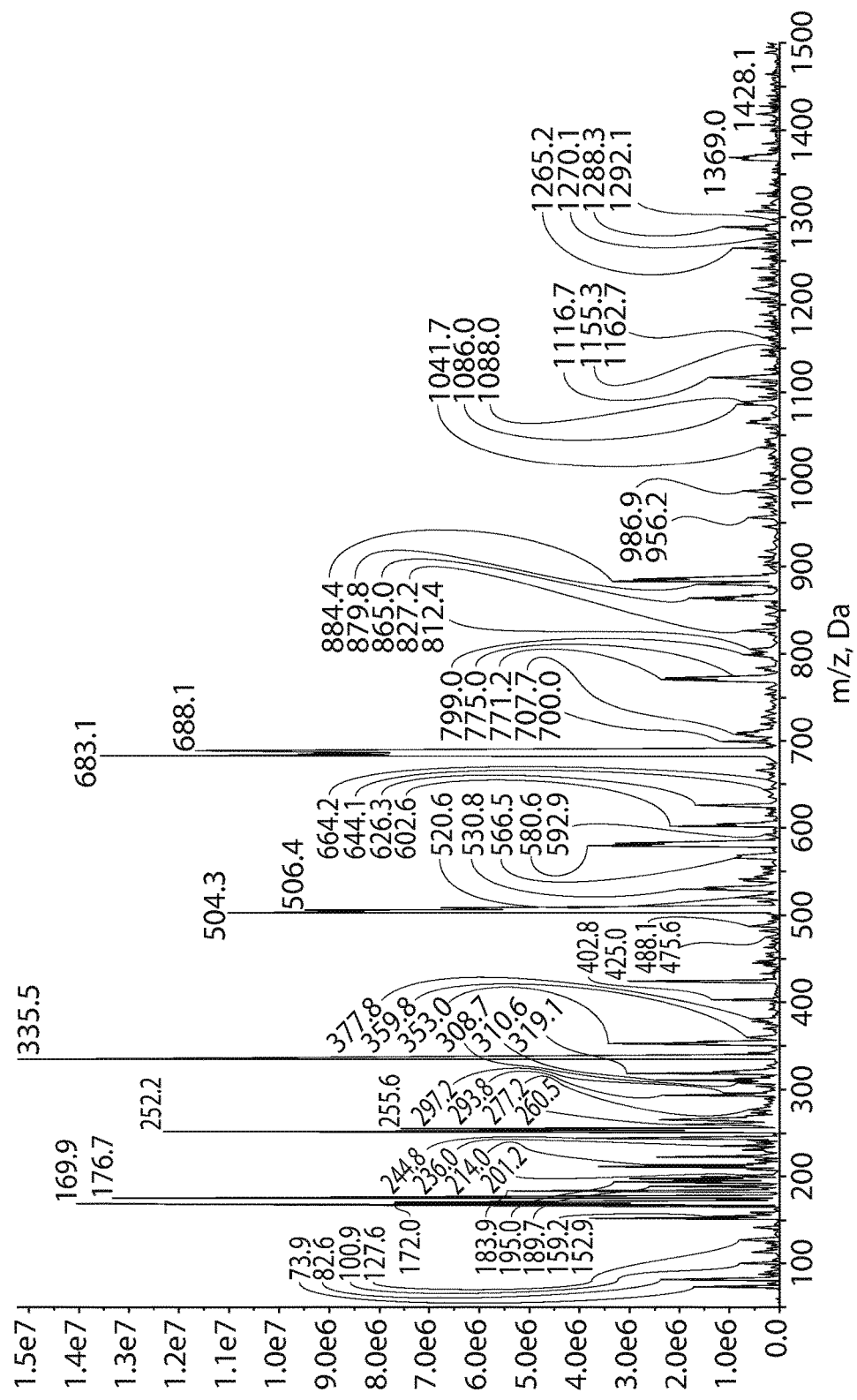
FIG. 1 depicts the mass spectrum (LC/MS) of the chlorhexidine cyclamate complex in methanol solution taken in positive ion mode.
Figure 2:
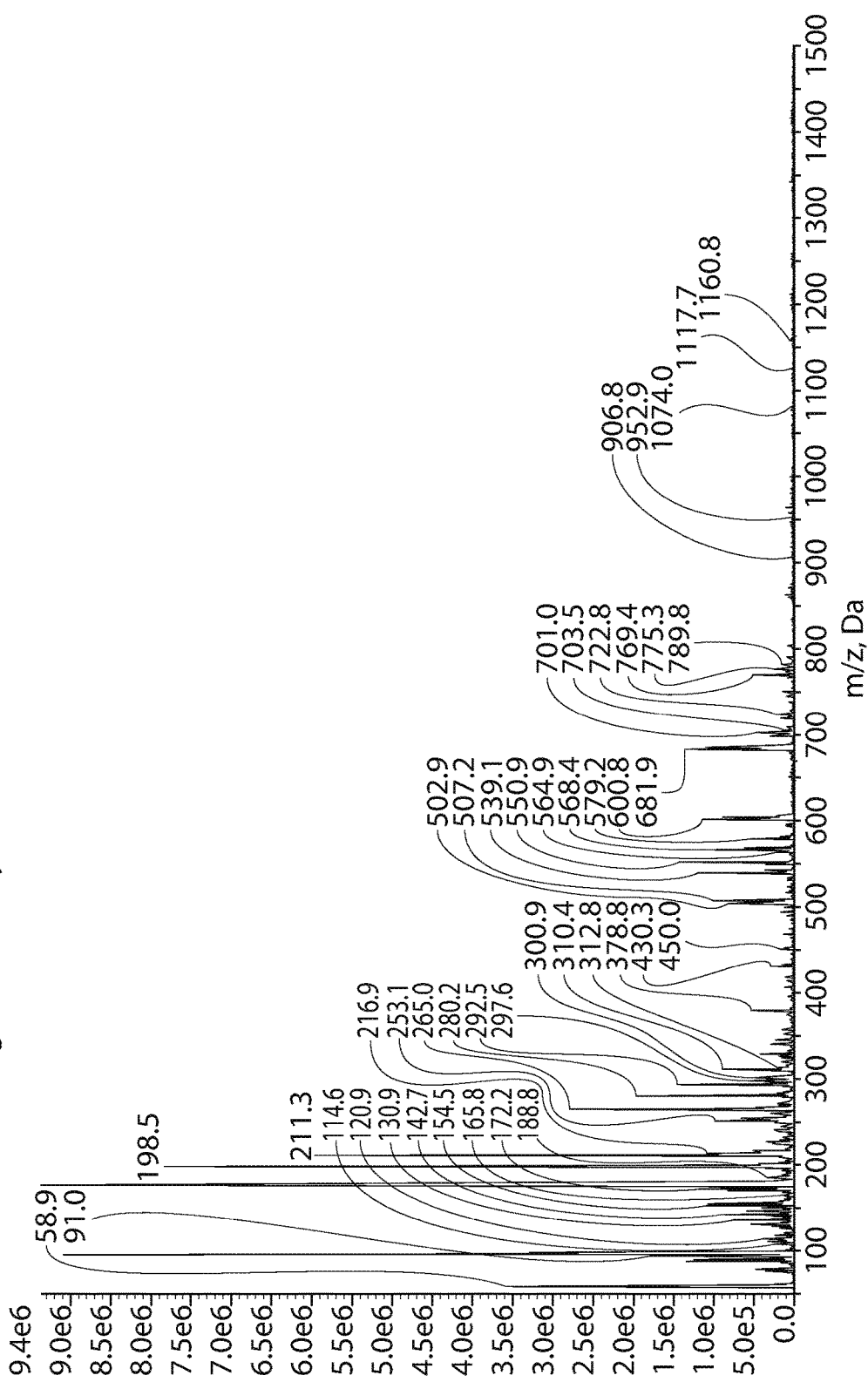
FIG. 2 depicts the mass spectrum (LC/MS) of the chlorhexidine cyclamate complex in methanol solution taken in negative ion mode.

The chlorhexidine-cyclamate complex was dissolved into methanol and the concentration about 200 ppm, which was transferred into the mass spectrometer directly for an analysis. Mass spectra of the complex in positive-ion mode and negative-ion mode are shown in FIGS. 1 and 2, respectively. FIG. 1 shows chlorhexidine molecular ion represented at m/z 504/506 in a chlorine pattern. Related fragments of chlorhexidine are represented at m/z 335, 252 and 170. Based on molecular analysis, the chlorhexidine adducts (i.e., cyclamate) at M+178 and M+178+178. These findings were confirmed in negative-ion mode as shown in FIG. 2.

Figure 3:
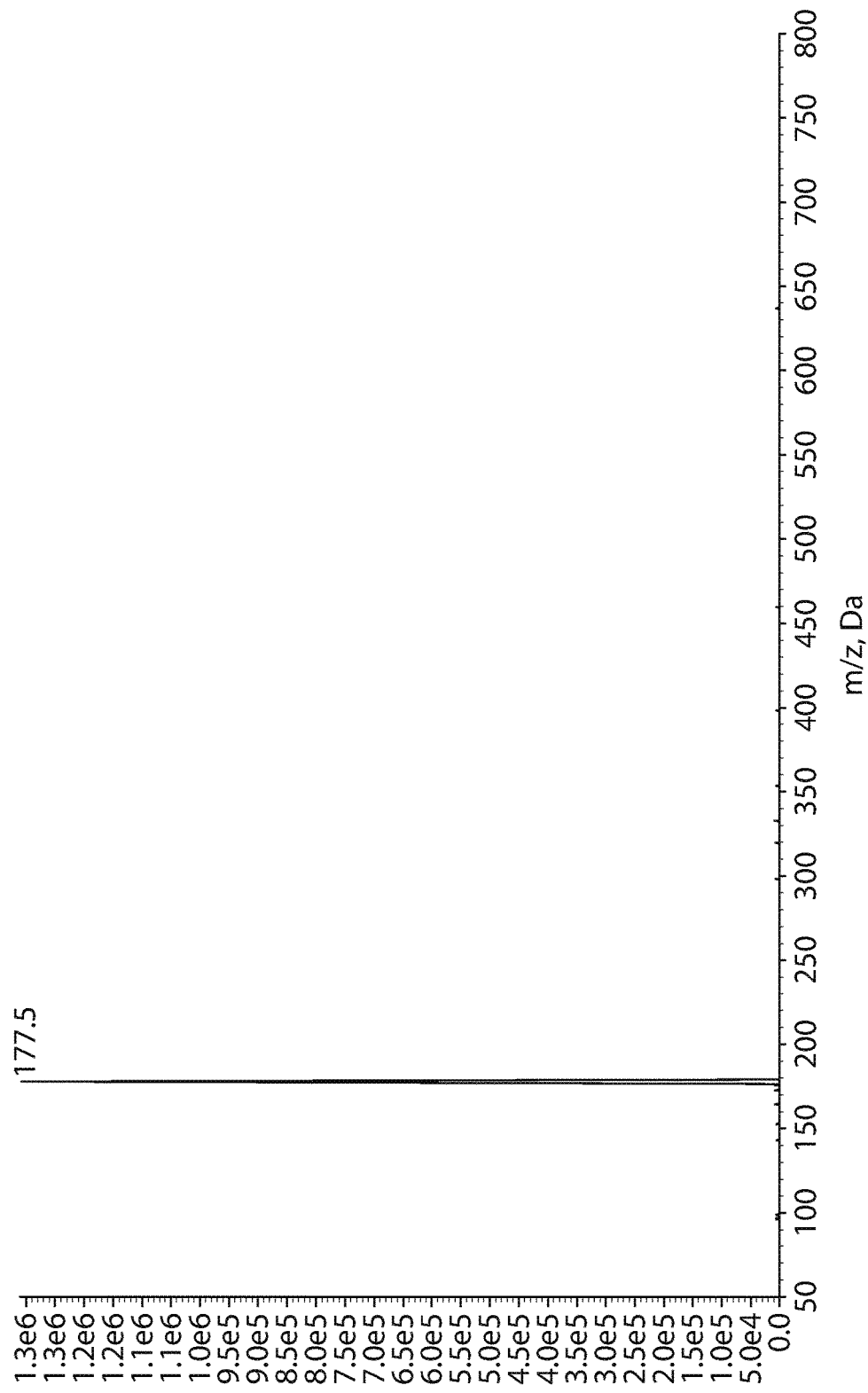
FIG. 3 depicts the tandem mass spectrum of cyclamate based on the parent ion represented at m/z: 682 in FIG. 2.
Figure 4:
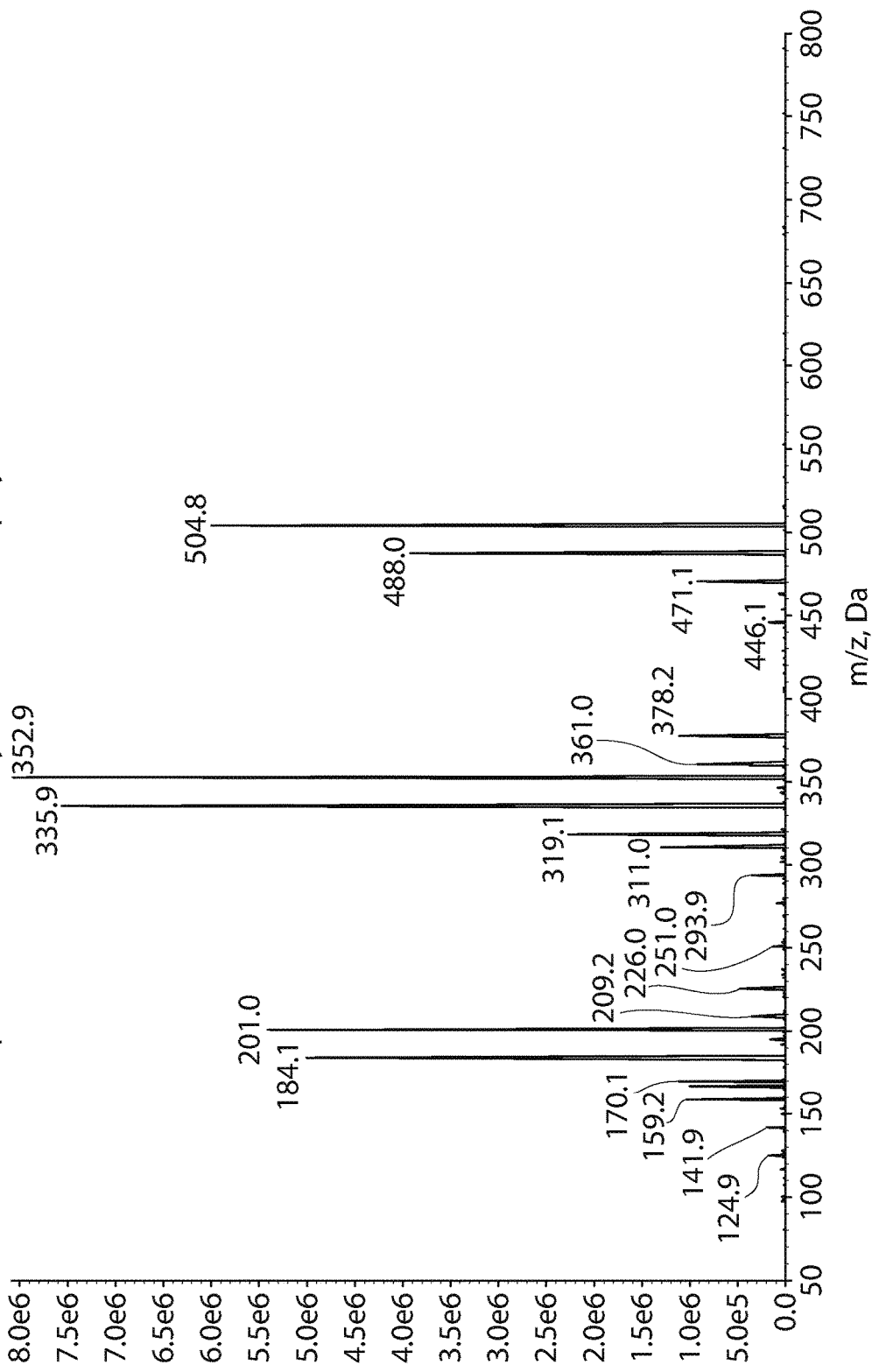
FIG. 4 depicts the tandem mass spectrum of cyclamate and chlorhexidine based on the parent ion represented at m/z: 684 in FIG. 1.
Figure 5:
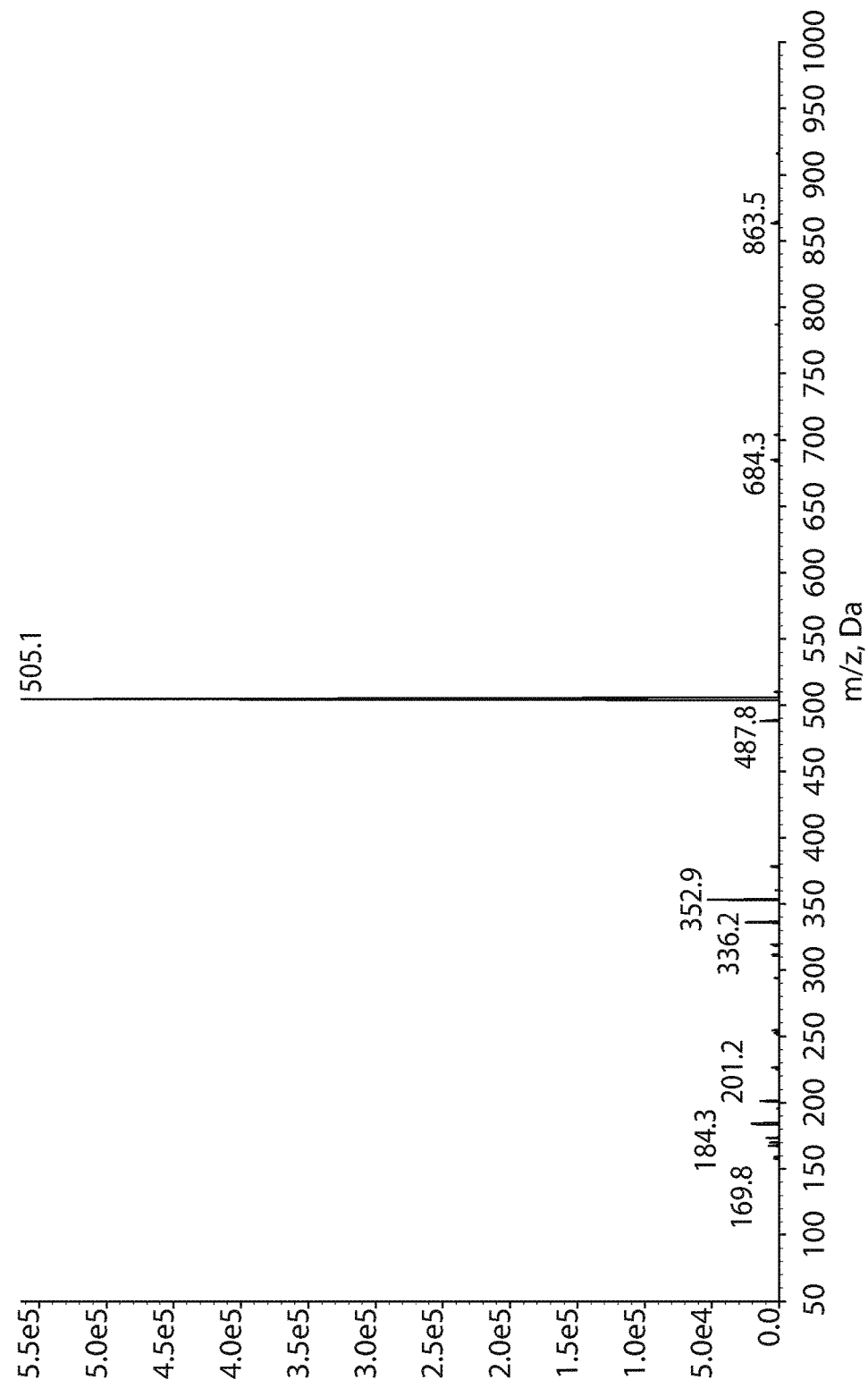
FIG. 5 depicts the tandem mass spectrum of cyclamate and chlorhexidine based on the parent ion represented at m/z: 863 in FIG. 1.

To confirm the adduct presence, tandem mass spectroscopy experiments were conducted in FIGS. 3, 4 and 5. FIG. 3, which was taken in negative-ion mode, shows fragmentation of cyclamate from the parent molecule represented at m/z 681.9 in FIG. 2. As the molecular weight of a cyclamate ion is 178.24 g/mol, the presence of the negative ion is clearly shown in FIG. 3. FIG. 4, taken in positive-ion mode, shows fragmentation of the parent molecule represented at m/z 684 in FIG. 1. FIG. 4 illustrates fragmentation of sodium cyclamate at m/z 201.04 and chlorhexidine at m/z 504.2. FIG. 5 was also taken in positive-ion mode and shows the fragmentation of the parent ion represented at m/z 863 of FIG. 1. FIG. 5 confirms fragmentation of sodium cyclamate at m/z 201.2, chlorhexidine at m/z 505.1, and chlorhexidine bound to two cyclamate ions at m/z 863.5.

Example 3: NMR Analysis of CHC $^1$H NMR measurements were performed on samples of CHC at a concentration of 1 wt. % in a deuterated DMSO solution. All NMR spectra were acquired on a Bruker Avance spectrometer (Bruker-Biospin, Billerica, MA, USA) with a 5 mm BBI probe operating at 500.0 MHz for $^1$H at 25° C. The $^1$H NMR resonance of the compounds were further assigned by means of homonuclear shift correlation 2-dimentional NMR (COSY).

Figure 6:
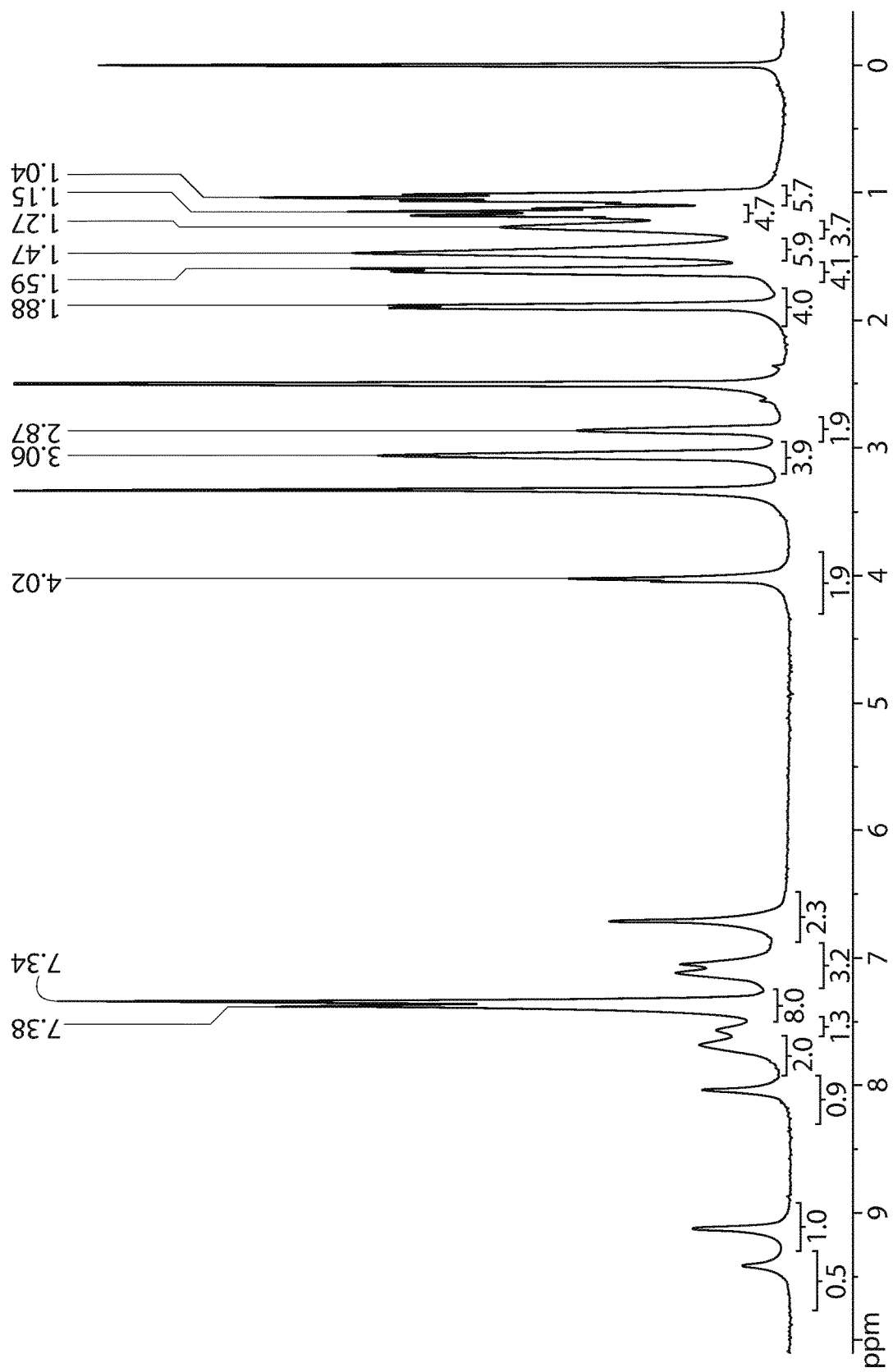
FIG. 6 depicts a $^1$H NMR spectrum of the chlorhexidine cyclamate complex crystal dissolved in deuterated DMSO.
Figure 7:
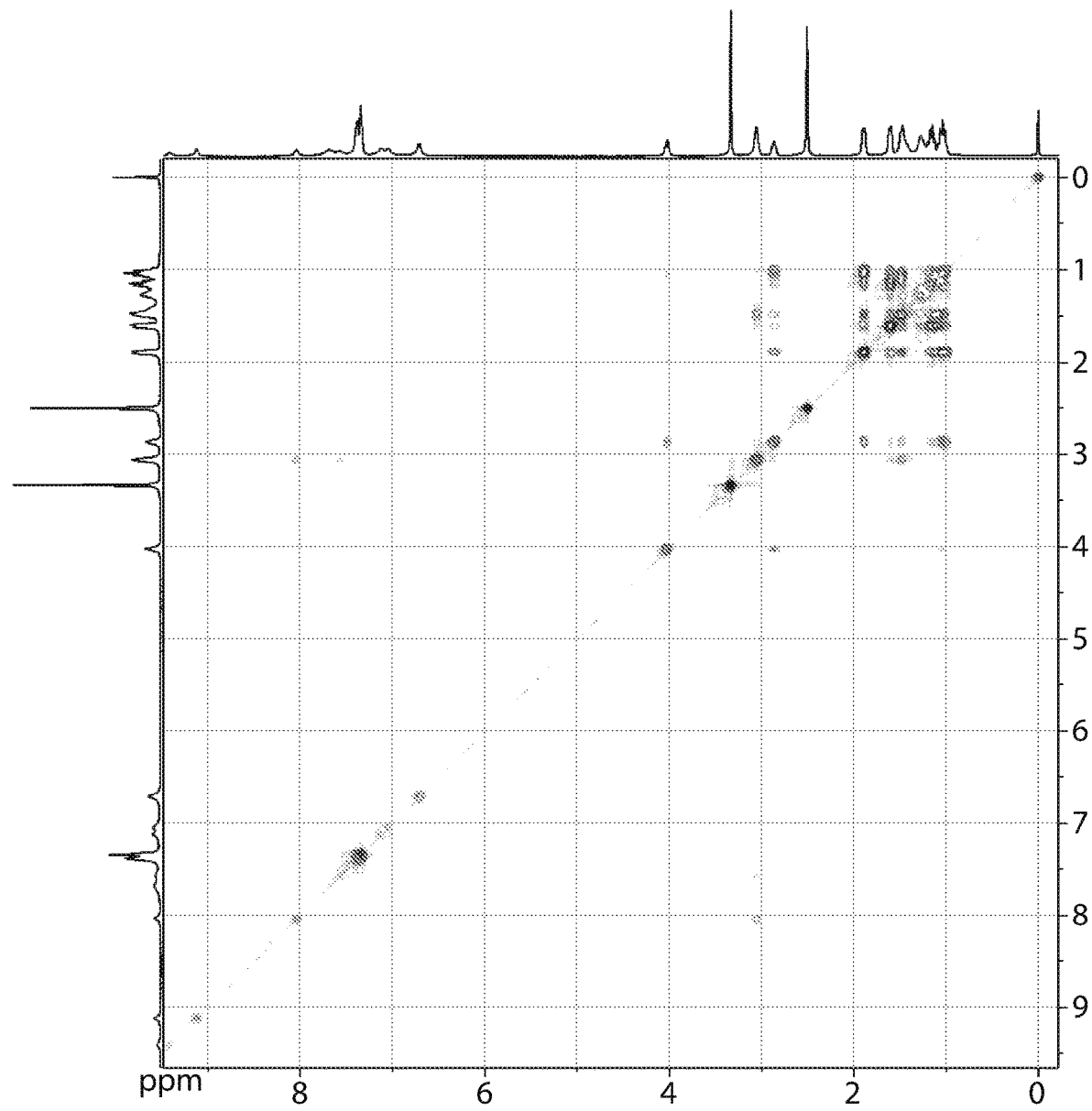
FIG. 7 depicts a $^1$H NMR COSY spectrum of the chlorhexidine cyclamate complex crystal dissolved in deuterated DMSO.
Figure 8:
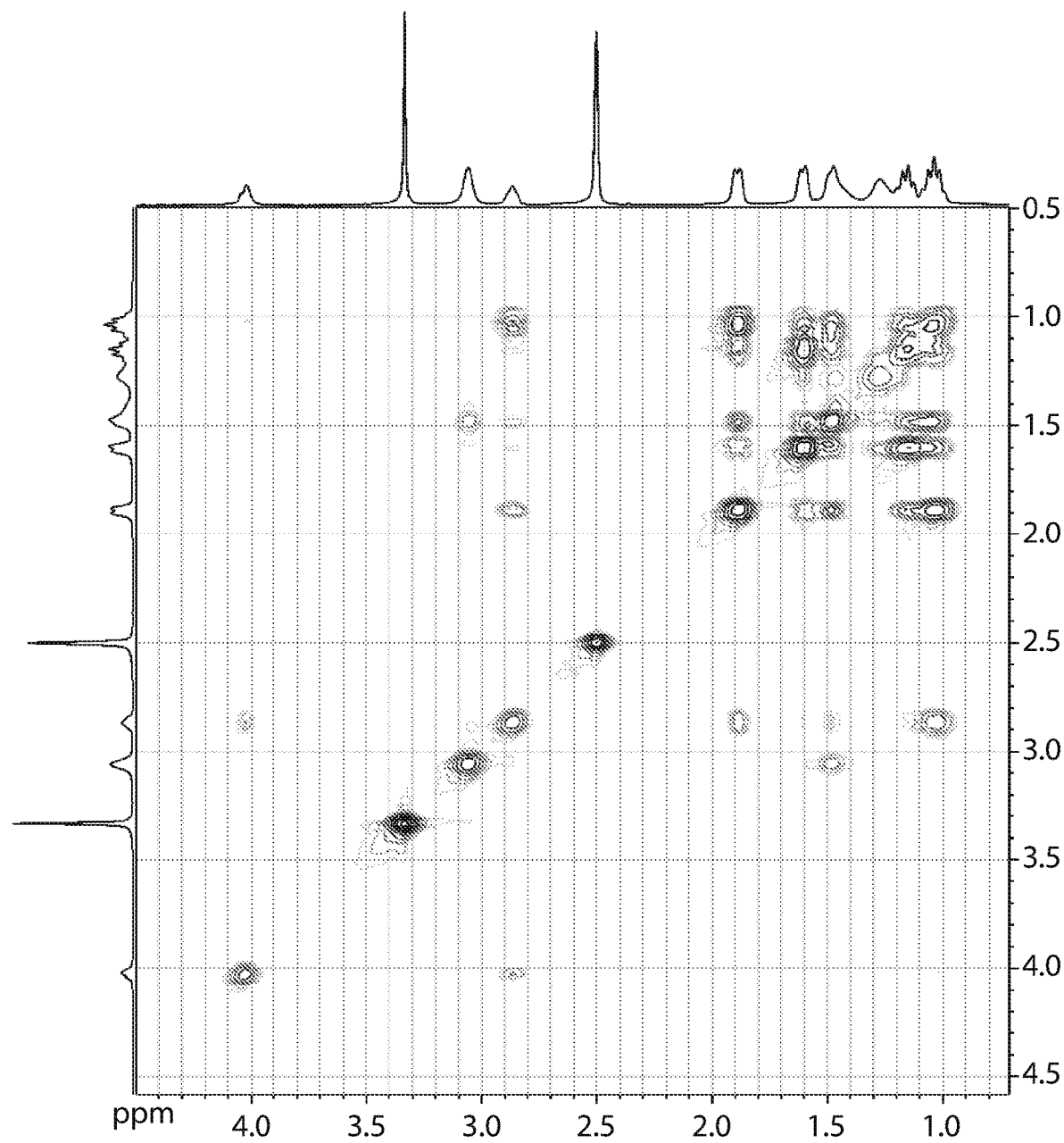
FIG. 8 depicts an enlarged section from FIG. 7.

$^1$H NMR spectroscopy is shown in FIG. 6 and related COSY sequences are shown in FIGS. 7 and 8. Each of these spectra confirmed that both chlorhexidine and cyclamate exist in the crystal dissolved in DMSO. The $^1$H NMR chemical shifts corresponding to specific protons of chlorhexidine and cyclamate were indicated in FIG. 6. Specifically, the peaks correspond to the chlorhexidine and cyclamate molecules as follows. According to peak integrals in FIG. 6, the stoichiometric ratio between chlorhexidine and cyclamate is 1:2.

Example 4: Determination of Crystal Structure

Single-crystal X-ray data was collected on a Bruker Smart Apex diffractometer equipped with an Oxford Cryostream low-temperature device and a fine-focus sealed-tube X-ray source Mo KR radiation, λ=0.71073 A°, graphite monochromated) operating at 45 kV and 35 mA, The structure demonstrates the compound crystallizes in P2$_1$/c space group. The empirical formula is: $[C_{22}H_{32}CL_2N_{10}][C_6H_{12}NO_3S]_2 \cdot H_2O$. The detailed structure is shown in FIG. 9. The chlorhexidine is connected to cyclamate and water by six types of hydrogen bonds. These results confirm the presence of a monohydrate crystalline form.

The data described herein confirms that chiorohexidine is released from the inventive complexes in a manner that maximizes its antibacterial activity.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present disclosure has been described with reference to exemplary embodiments. Although a few embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. A chlorhexidine-cyclamate complex having a formula $[C_{22}H_{32}Cl_2N_{10}][C_6H_{12}NO_3S]_2$, wherein the chlorhexidine-cyclamate complex was formed as a precipitate in an aqueous solution.

2. The chlorhexidine-cyclamate complex of claim 1 in crystalline form.

3. The chlorhexidine-cyclamate complex of claim 1, wherein the complex is anhydrous.

4. The chlorhexidine-cyclamate complex of claim 1, wherein the complex is in the form of a hydrate, hemihydrate or polyhydrate.

5. The chlorhexidine-cyclamate complex of claim 4, wherein the complex has the formula $[C_{22}H_{32}Cl_2N_{10}][C_6H_{12}NO_3S]_2 \cdot H_2O$.

6. The chlorhexidine-cyclamate complex of claim 1, that is formed from a mixture of chlorhexidine and sodium cyclamate in a molar ratio of chlorhexidine:sodium cyclamate of 1:1 to 1:3.

7. The chlorhexidine-cyclamate complex of claim 1, in crystalline form in a P2$_1$/c space group.

8. The chlorhexidine-cyclamate complex of claim 1, having a structure wherein a biguanide moiety of the chlorhexidine cation is coordinated by two cyclamate ligands and a water ligand.

9. The chlorhexidine-cyclamate complex of claim 1, which has been crystallized in an aqueous solution.

10. The chlorhexidine-cyclamate complex of claim 9 wherein the aqueous solution contains 84 wt. % water, 3 wt. % ethanol, and 10 wt. % glycerin.

11. A method of making the chlorhexidine-cyclamate complex of claim 1, comprising combining chlorhexidine and sodium cyclamate in an aqueous solution and precipitating the complex.

12. The method of making of claim 11, wherein the aqueous solution further comprises an alcohol.

13. The method of making of claim 11, wherein the aqueous solution further comprises ethanol.

14. The method of making of claim 12, wherein the aqueous solution further comprises one or more of glycerin, sodium fluoride, xylitol, a surfactant and an antibacterial agent.

* * * * *